United States Patent [19]
Koziol

[11] Patent Number: 5,364,388
[45] Date of Patent: * Nov. 15, 1994

[54] BEAM DELIVERY SYSTEM FOR CORNEAL SURGERY

[76] Inventor: Jeffrey E. Koziol, 1211 S. Arlington Heights Rd., Arlington Heights, Ill. 60005

[*] Notice: The portion of the term of this patent subsequent to Dec. 24, 2008 has been disclaimed.

[21] Appl. No.: 944,431

[22] Filed: Sep. 14, 1992

Related U.S. Application Data

[63] Continuation-in-part of Ser. No. 812,163, Dec. 23, 1992, which is a continuation of Ser. No. 598,793, Oct. 17, 1990, Pat. No. 5,074,859, which is a continuation of Ser. No. 464,637, Jan. 5, 1990, abandoned, which is a continuation of Ser. No. 176,765, Apr. 1, 1988, abandoned.

[51] Int. Cl.$^5$ .................................................. A61N 5/02
[52] U.S. Cl. .................................... 606/5; 606/10; 606/13; A61A/5/02
[58] Field of Search ............................. 606/3-6, 606/10-13, 19

[56] References Cited

U.S. PATENT DOCUMENTS

| | | | |
|---|---|---|---|
| 3,821,510 | 6/1974 | Muncheryan | 219/121.79 |
| 3,931,491 | 1/1976 | Stumpf | 219/121.84 |
| 4,002,877 | 1/1977 | Banas | 219/121.84 |
| 4,028,525 | 6/1977 | Mominee et al. | 219/121.78 |
| 4,315,130 | 2/1982 | Inagaki et al. | 219/121.73 |
| 4,356,375 | 10/1982 | Josephy et al. | 219/121.73 |
| 4,370,540 | 1/1983 | Davis et al. | 219/121.6 |
| 4,409,979 | 10/1983 | Roussel et al. | 128/303.1 |
| 4,461,294 | 7/1984 | Baron | 128/303.1 |
| 4,518,232 | 5/1985 | Dagenais | 219/121.74 |
| 4,648,400 | 3/1987 | Schneider et al. | 128/303.1 |
| 4,658,109 | 4/1987 | Honeycutt et al. | 219/121.73 |
| 4,665,913 | 5/1987 | L'Esperance, Jr. | 128/303.1 |
| 4,669,466 | 6/1987 | L'Esperance | 128/303.1 |
| 4,712,543 | 12/1987 | Baron | 128/303.1 |
| 4,720,619 | 1/1988 | Mattel et al. | 219/121. 77 |
| 4,724,522 | 2/1988 | Beljorod | 128/303.1 |
| 4,729,372 | 3/1988 | L'Esperance | 219/121.74 |
| 4,732,148 | 3/1988 | L'Esperance, Jr. | 128/303.1 |
| 4,907,586 | 3/1990 | Bille et al. | 606/5 |
| 5,074,859 | 12/1991 | Koziol | 606/5 |

FOREIGN PATENT DOCUMENTS

| | | | |
|---|---|---|---|
| 2594686 | 8/1987 | France | 128/303.1 |
| 8707165 | 12/1987 | WIPO | 128/303.1 |

OTHER PUBLICATIONS

"Excimer Laser Ablation of Cornea and Lens", Puliafito et al, Ophthalmology, vol. 92, No. 9, Jun. 1985, pp. 741-748.

"Corneal Surgery", Girard, vol. 2, 1981, pp. 106-171.

"Response of the Corneal Epithelium to KrF Excimer Laser Pulses", J. Taboda et al, Health Physics, vol. 40, May 1981, pp. 677-683.

Primary Examiner—David M. Shay
Attorney, Agent, or Firm—Roylance, Abrams, Berdo & Goodman

[57] ABSTRACT

An apparatus and method for delivering radiant energy beams onto an area of a cornea in a line focus to create a linear incisions. The radiant energy beams may be focused in a linear configuration onto the external surface of the cornea or onto intrastromal areas of the cornea of an eye to ablate the cornea in a radial slot, circumferential curved slot, or lenticular pattern, and thereby modify its curvature and refractive power. The apparatus includes an array of central reflectors and an assembly of peripheral reflectors. Each central reflector is associated with a respective peripheral reflector so that a beam reflected by the central reflector is intercepted by its associated peripheral reflector and is again reflected to precisely incise either external or internal areas of the cornea. Each peripheral reflector has a curved reflective surface to provide a line focus on the cornea, including both rectilinear and curvilinear line focus to create radial and circumferential curved incisions. In a modified embodiment, the assembly of peripheral reflectors and the array of central reflectors rotate to permit lathing of the cornea.

53 Claims, 6 Drawing Sheets

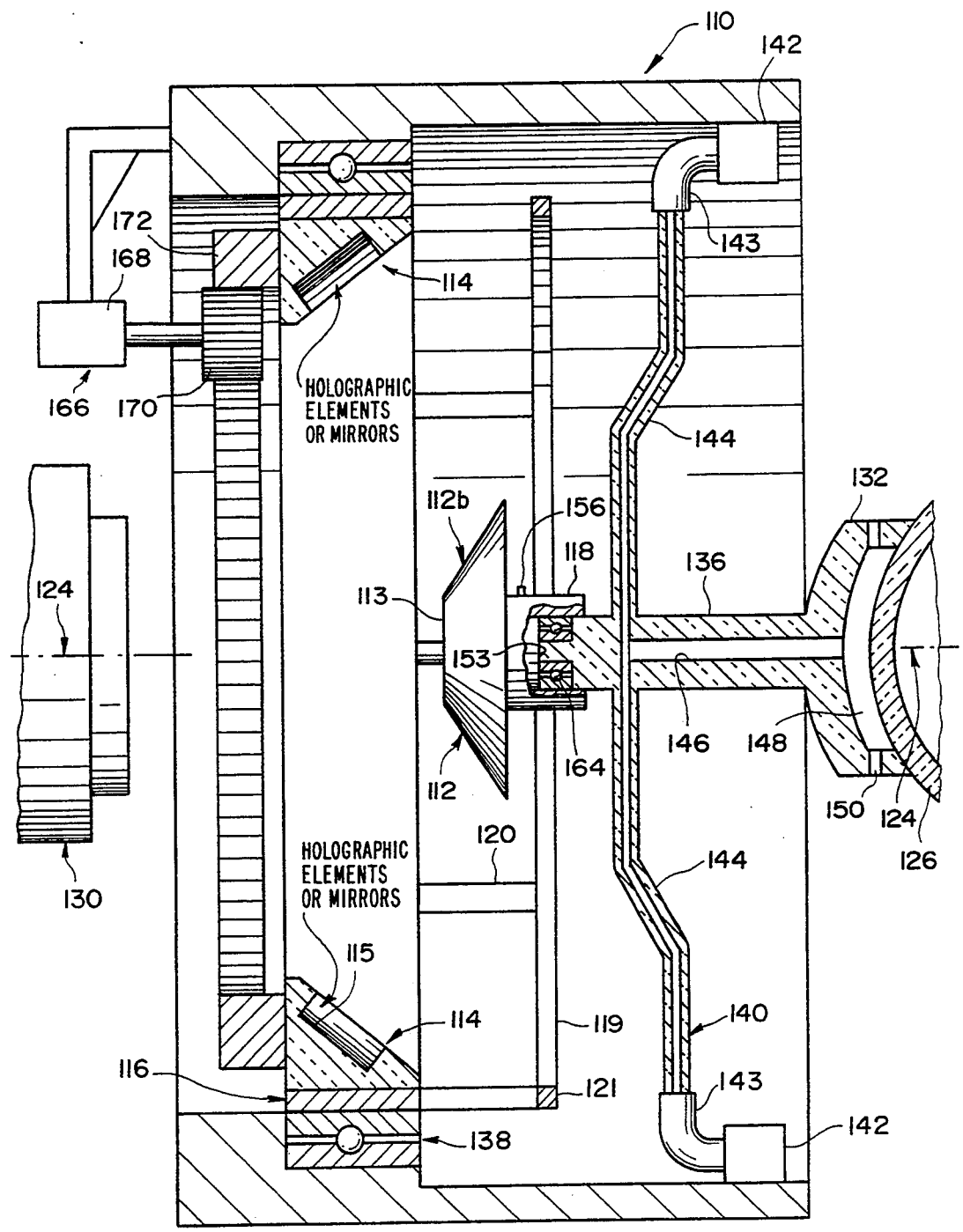

BEAM DELIVERY SYSTEM FOR CORNEAL SURGERY

RELATED APPLICATIONS

This is a continuation-in-part application of Ser. No. 07/812,163 filed on Dec. 23, 1992, which is a continuation of Ser. No. 07/598,793 filed on Oct. 17, 1990, now U.S. Pat. No. 5,074,859, which is a continuation of Ser. No. 07/464,637 filed on Jan. 5, 1990, now abandoned, which is a continuation of Ser. No. 07/176,765 filed on Apr. 1, 1988, now abandoned.

FIELD OF THE INVENTION

The invention relates to an apparatus for delivering radiant energy beams onto the cornea of an eye. More specifically, the invention relates to an array of central reflectors for intercepting a radiant energy beam and reflecting and splitting the beam along several paths to an assembly of peripheral reflectors radially spaced therefrom, which in turn focus and reflect the beams onto the cornea in line configurations. The central reflector array and the peripheral reflector assembly can be rotated as a single unit relative to the eye for scanning operations. The invention when used in a stationary position can ablate the cornea via simultaneously applied radial or circumferential incisions, and when rotated can re-profile the cornea via photolathing.

BACKGROUND OF THE INVENTION

The use of high intensity light sources such as lasers for cutting and reshaping eyes has expanded in recent years in part due to the superior precision, controllability and safety which such cutting technology offers over other cutting technologies, such as mechanical cutting of the eye. One type of ophthalmic surgical procedure for which high-intensity light radiation is particularly well suited is the radial keratotomy procedure in which a number of radial incisions are made on the cornea of the eye to change the curvature of the cornea.

Several methods and apparatus for performing radial keratotomies with lasers have been proposed. See, for example, U.S. Pat. No. 4,648,400 to Schneider et al; and U.S. Pat. No. 4,665,913 to L'Esperance, Jr. Schneider et al describe the use of lasers to selectively ablate the cornea of the eye by directing the laser beam through a generally planar mask having radial slots. The radial slots of the mask permit portions of the laser beam to pass through the mask and incise the cornea in a pattern of circumferentially spaced radial incisions.

Lasers have also been used to ablate an annular portion of the cornea by scanning or variably attenuating the laser beam. Such scanning changes the front surface of the cornea to a different optical curvature, thereby changing the refraction of the eye. See, for example, U.S. Pat. No. 4,669,466 to L'Esperance.

In such an application, it is desirable to deliver uniform beam energy along the curved scanning path. However, since the cornea presents a convexly curved surface to the laser beam, the outer circumferential portions of the cornea lie at further distances from the beam source than those portions at or near the center of the cornea. Thus, the laser beam incidents the cornea with a different angle along the cornea's constantly changing surface which causes variation of the energy density of the laser beam in a direction perpendicular to the corneal surface.

Using a mask to produce corneal incisions does not focus the beam on the corneal surface but merely projects the beam toward the surface.

Additionally, the energy of the laser beam may not be distributed uniformly due to the position of the mask relative to the beam. A non-uniform distribution of energy results in differing depths of the radial incisions, leading to an improper restructuring of the curvature of the cornea.

More recently, laser systems have been developed to ablate intrastromal areas of a cornea without ablating or piecing the external surface of the cornea. These laser systems focus the lower beams as a spot on either external or intrastromal areas of the cornea to be ablated. Thus, to create a linear incision, the laser must ablate a plurality of spots along the line of incisions. An example of a laser system employing spot focus ablation is disclosed in U.S. Pat. No. 4,907,586 to Bille et al, which is hereby incorporated herein by reference.

SUMMARY OF THE INVENTION

Accordingly, a primary object of the present invention is to provide an apparatus and method for delivering radiant energy from a radiant energy source in a line focus onto an area of the cornea to create linear incisions, including rectilinear and curvilinear incisions.

A further object of the invention is to provide an apparatus and method which can simultaneously direct a number of radiant energy beams onto an eye from a single source.

A further object of the invention is to provide an apparatus and method which can direct radiant energy onto an eye so as to lathe the eye and for a lenticular ablation.

An additional object of the invention is to provide an apparatus and method for delivering radiant energy onto an eye which minimizes the energy needed to incise the cornea to a desired depth via focusing of the radiant energy.

Another object of the invention is to provide an apparatus and method for controlling radiant energy to produce optical changes in an eye and maintain substantially constant incision depth across the incision Another object of the invention is to provide an apparatus and method of conducting corneal surgery via focusing laser light and thus concentrate the laser energy 100 to 10,000 times to permit use of low cost lasers such as a frequency modified YAG laser.

The foregoing objects are basically attained by providing an apparatus for delivering radiant energy beams onto the cornea of an eye centered on a main optical axis, the combination comprising a source of a radiant energy beam aimed along the main optical axis; a support; an array of discrete central reflectors arranged about the main optical axis for intercepting the radiant energy beam incident thereon, splitting the beam into a plurality of beam portions, and reflecting each beam portion outwardly of the main optical axis; a first member coupled to the support and the array of central reflectors for coupling the central reflectors to the support; an assembly of discrete peripheral reflectors outwardly spaced from the central reflectors, each peripheral reflector intercepts one of the reflected beam portions from an associated central reflector and directs the intercepted beam portion generally along the main optical axis and incident onto the cornea; and a second member coupled to the support and the peripheral reflectors for coupling the peripheral reflectors to the support, each of the peripheral reflectors including a mechanism for focusing the intercepted beam portion onto an area on the cornea separate and discrete from the incidence of the other of the intercepted beam portions on the cornea and in a linear configuration.

The foregoing objects are also attained by providing a method of ablating a cornea via a radiant energy beam comprising the steps of aligning a source of a radiant energy beam and the cornea along a main optical axis, emitting the radiant energy beam from the source, splitting the beam into a plurality of beam portions and reflecting those beam portions outwardly of the main optical axis, and reflecting the outwardly directed beam portions to produce output beam portions incident on the cornea.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

Referring now to the drawings which form a part of this original disclosure,

FIG. 9 is a cross-sectional side view of another modification of the apparatus of FIG. 1, having modified peripheral reflectors for ablating circumferentially curved lines either on the external surface of the cornea, or on intrastromal areas of the cornea without disturbing, coagulating or ablating the tissue between the peripheral reflectors and the intrastromal areas to be ablated;

DETAILED DESCRIPTION OF PREFERRED EMBODIMENTS

Figure 1:
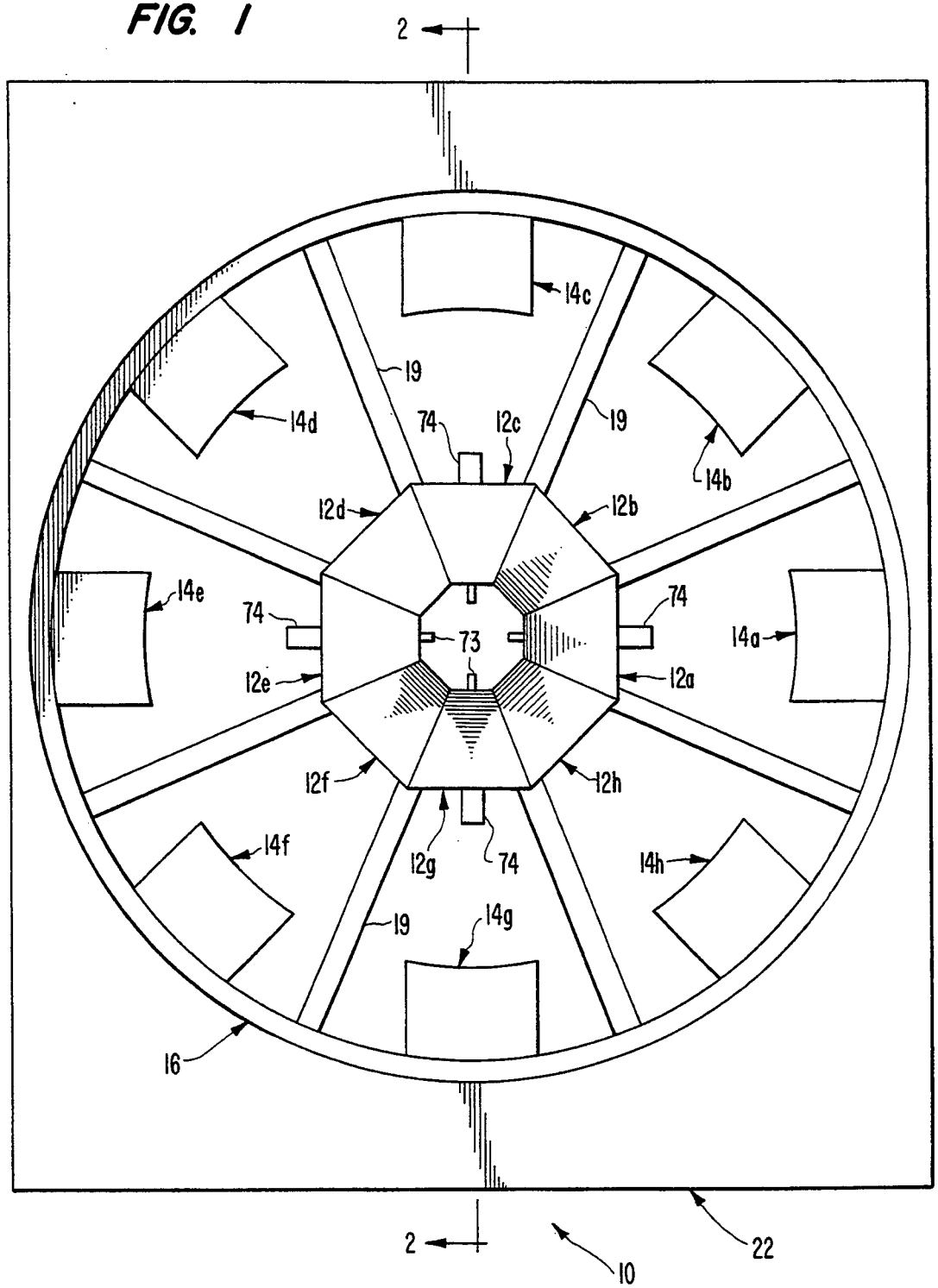
FIG. 1 is a front plan view of the beam delivering apparatus of the present invention, showing an array of central reflectors, each having an associated peripheral reflector radially and axially spaced from it.
Figure 2:
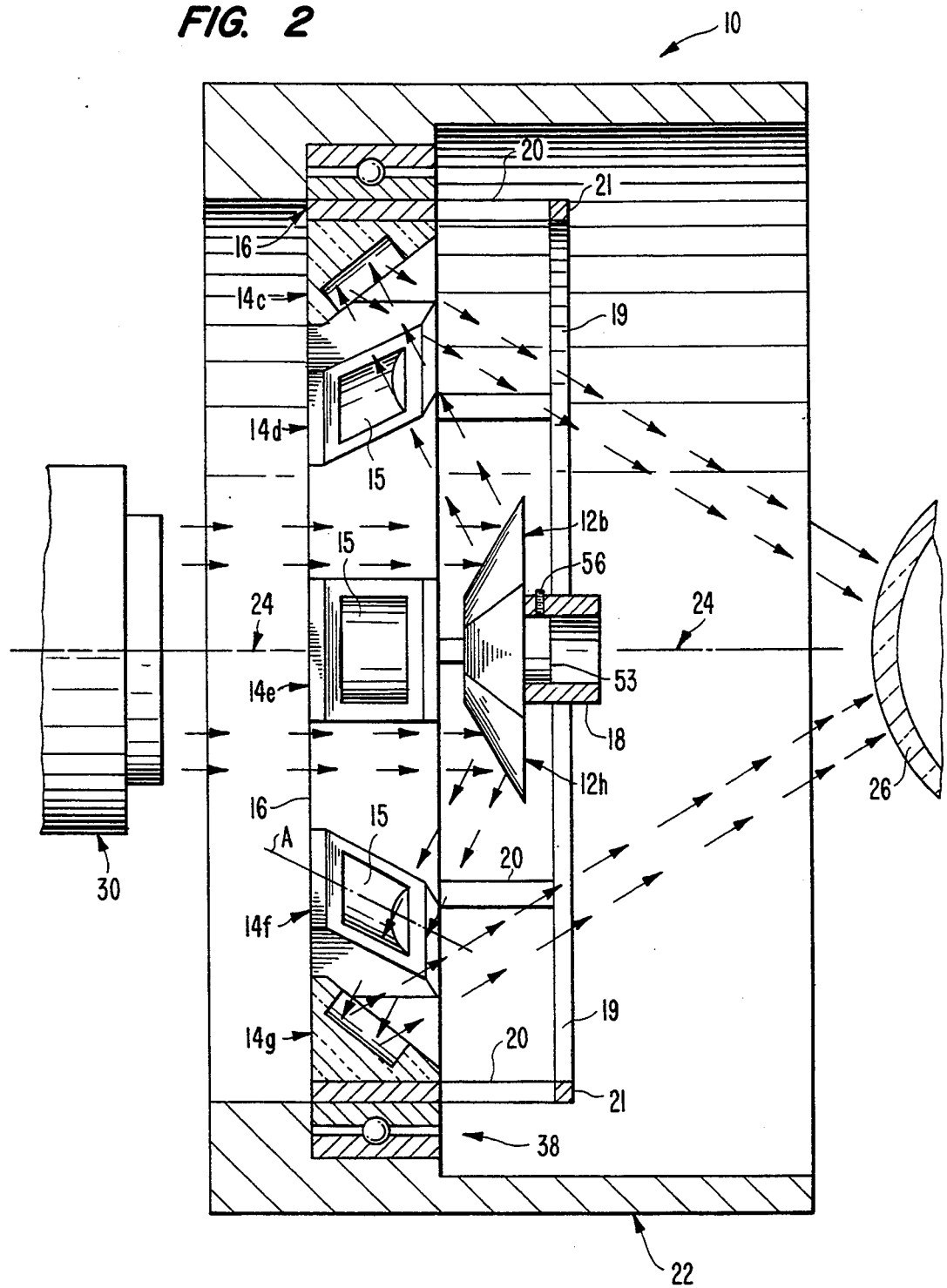
FIG. 2 is a cross-sectional side view of the beam directing apparatus of FIG. 1, taken along line 2—2 in FIG. 1 and showing the apparatus aligned between a laser beam source and the cornea of an eye.

As seen in FIG. 1, a beam delivering apparatus 10 for focusing beams of radiant energy in a linear configuration is illustrated in accordance with a first embodiment of the present invention, and basically includes an annular array of central reflectors 12a–h and an annular assembly of peripheral reflectors 14a–h. Peripheral reflectors 14a–h are rigidly coupled to a rim 16. As seen in FIG. 2, rim 16 is rigidly coupled to a hub 18 by radial spokes 19, axial rods 20 and a ring 21. Central reflectors 12a–h are coupled to hub 18.

Beam delivering apparatus 10 is rotatably supported within a support or frame 22 about a main optical axis 24 which passes through the center of a cornea 26 of an eye. A laser beam source 30, such as a frequency modified YAG laser for ablating external surface areas of the cornea or a frequency-doubled YAG laser for ablating intrastromal areas of the cornea, is positioned to emit a beam along axis 24 and against central reflectors 12a–h. These reflectors split and reflect the beam onto peripheral reflectors 14a–h which then focus and reflect the split beams onto cornea 26.

Beams delivering apparatus 10 can be modified in a number of ways to adapt it for use in particular types of ophthalmic surgery. For example, beam delivering apparatus 10 can be modified to perform radial keratotomy operations on the external surface of cornea 26 or on intrastromal areas of cornea 26.

Referring now more specifically to the construction and orientation of central reflectors 12a–h and peripheral reflectors 14a–h for the radial keratotomy operation, a number of equal sized central reflectors 12a–h are provided and, preferably, the number of central reflectors is an even number more than two and less than 16, such as eight. As shogun in FIG. 1, eight equally sized central reflectors 12a–h are rigidly coupled to one another along their sides in a octagonal array. As seen in FIG. 2, each central reflector 12a–h is oriented to present a slanted, outwardly facing flat surface to the beam emanating from beam source 30. The angle of each surface is about 50°–60° to axis 24.

Each peripheral reflector 14a–h is associated with one of central reflectors 12a–h and is oriented so that its reflective surface 15, which is curved and preferably semi-cylindrical about central axis A as seen in FIG. 2 and angled at about 40°–50° to axis 24, intercepts the beam reflected radially, outwardly by its associated central reflector. Axis A intersects main optical axis 24 at an acute angle of about 40°–50°. Additionally, each peripheral reflector is oriented so as to reflect the intercept beam axially and radially inward and to focus the beam into line focus either onto the external surface of cornea 26 or onto an intrastromal area of the cornea. The reflective surfaces of the central and peripheral reflectors can be mirrors or other reflective material.

For example, the peripheral reflectors can be replaced with holographic elements.

Figure 6:
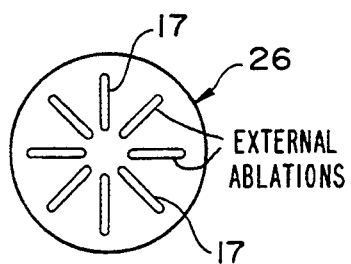
FIG. 6 is a schematic view of a cornea having radial incisions produced by a laser bee source in conjunction with the apparatus of FIGS. 1-3.
Figure 8:
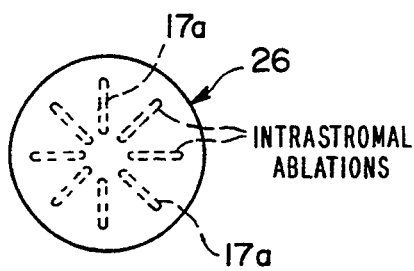
FIG. 8 is a schematic view of a cornea having intrastromal radial incisions produced by a laser beam source in conjunction with the apparatus of FIGS. 1-3.

As schematically shown in FIG. 6, a number of radial incisions 17 are cut via photoablation in the external surface of cornea 26 during the radial keratotomy operation. Alternatively, a number of radial, intrastromal incisions 17a can be cut via photoablation in intrastromal areas of cornea 26 during a radial keratotomy operation, as schematically illustrated in FIG. 8.

Beam delivering apparatus 10 can be used to produce the external or intrastromal incisions simultaneously. As seen in FIG. 1, each central reflector 12a-h intercepts the beam and reflects the beam towards its associated peripheral reflector. Central reflectors 12a-h are preferably rotatably coupled to hub 18 via an axle 53 fitting into the hub 18 and a screw adjustment assembly including three set screws 56 to lock the reflectors relative to hub 18. Central reflectors 12a-h can be moved as a single unit relative to hub 18 and the adjustment screws 56 can then be operated to adjust and fix the relative position of the central reflectors relative to the peripheral reflectors.

The combination of central and peripheral reflectors including the rim 16, hub 18, spokes 19, rods 20 and ring 21 are supported for rotation relative to frame 22 via ball bearing assembly 38, which is coupled to the frame and to rim 16. Thus, the angular position of the reflectors relative to the cornea and axis 24 can be varied. This allows angular placement as desired of either external incisions 17 on the cornea or intrastromal incisions 17a in the cornea.

The operation of beam delivering apparatus 10 during a simple radial keratotomy operation is as follows. Cornea 26 is immobilized by appropriate means and laser beam source 30 is positioned to emit a beam along main optical axis 24, which passes through the center of cornea 26. Beam directing apparatus 10 is positioned between beam source 30 and cornea 26 and is appropriately spaced from cornea 26 so that the beams reflected by the central and peripheral reflectors ablate cornea 26 in a pattern comprising separate and discrete areas of ablation shown in FIG. 6 or FIG. 8. Once beam directing apparatus 10 is positioned, a test beam can be emitted to test the alignment of the beams on cornea 26. Beam source 30 is then operated to emit a radiant energy beam, such as a laser beam, which travels along axis 24, encounters the central reflectors 12a-h, is split and radially reflected against peripheral reflectors 14a-h and is then again radially reflected and focused either onto the external surface of cornea 26 to simultaneously make external incisions 17 or onto intrastromal areas of cornea 26 to simultaneously make intrastromal incisions 17a.

Figure 3:
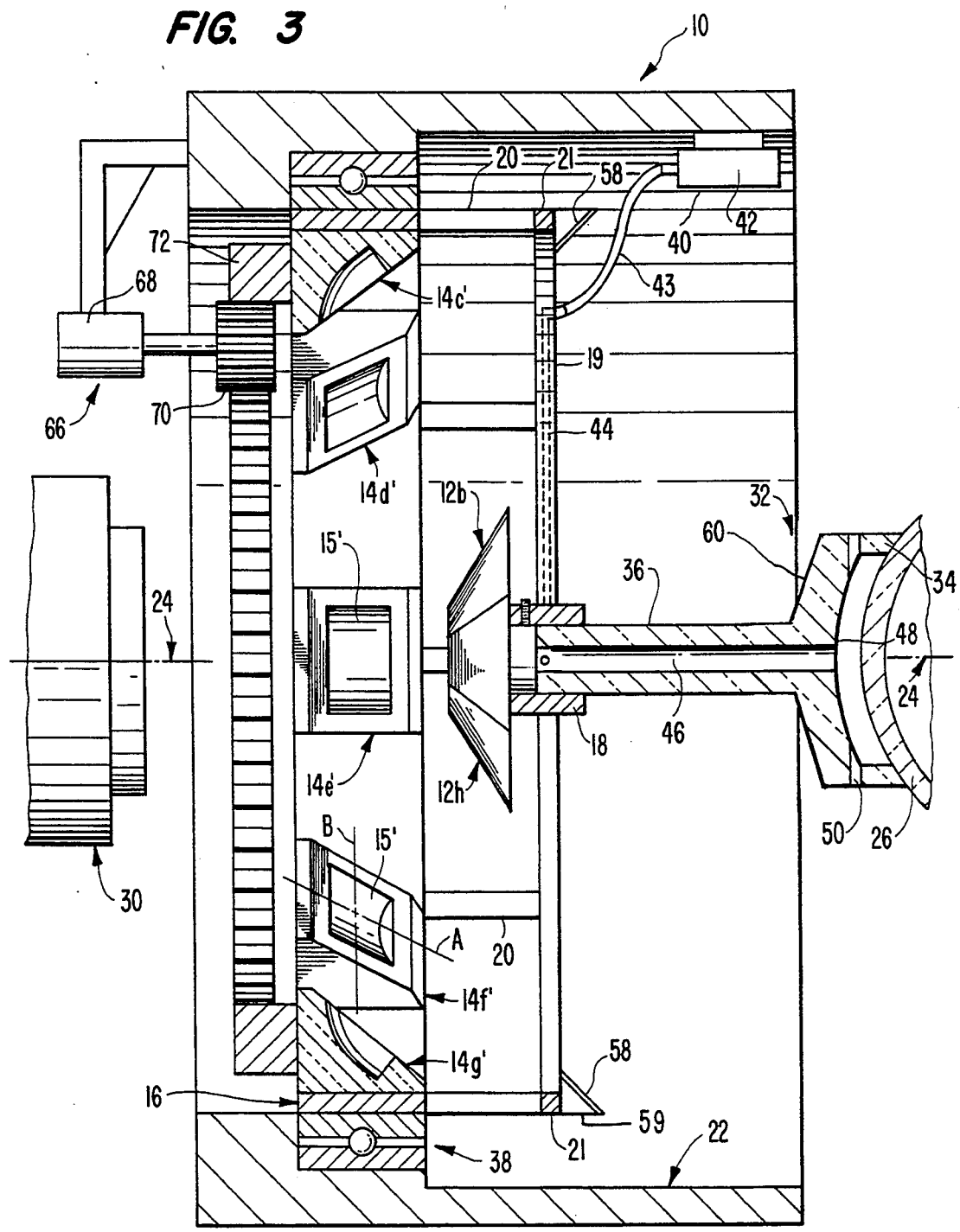
FIG. 3 is a cross-sectional side view of a modification of the apparatus of FIG. 1, having a gas conduit system for delivering gas to the ablated surface of the eye, a cornea alignment receptacle for positioning the cornea and a detection system for detecting the beam power density distribution as well as a motive assembly to rotate the reflectors.

Embodiment of FIG. 3

With reference especially to FIG. 3, beam delivering system 10 can have added to it an eye positioning device 32, coaxial with main optical axis 24 and coupled to hub 18. Eye positioning apparatus 32 has a concave surface 34, preferably having a radius of curvature the same as the average radius of curvature of a cornea, so that cornea 26 can be pressed against concave surface 34 and steadied in a fixed position during the eye operation. Eye positioning apparatus 32 is coupled via a connecting stem 36 to hub 18.

Eye positioning device 32 is preferably constructed of material which is transparent to the beam emitted by beam source 30 and permits complete through transmission of the beams reflected from the central and peripheral reflectors towards cornea 26.

Beam delivering apparatus 10 and eye positioning apparatus 32 can be provided with a gas or fluid conduit system 40 for delivering selected gases to the cornea 26 during ablation. Gas conduit system 40 includes a gas supply means 42 to supply gas along a tube 43 and a conduit 44 mounted within one of the spokes 19. Conduit 44 communicates with an axial conduit 46 within eye positioning apparatus 32 and axial conduit 46 communicates with a substantially semihemispheric recess 48 defined by concave surface 34. Recess 48 communicates with conduit 46 and cornea 26 and has outlets 50 for exhausting gases which have contacted cornea 26.

An inert gas such as argon can be supplied by gas conduit system 40 to contact cornea 26 and remove debris and other by-products of the surgical operation. Additionally, a gas or liquid having a cold temperature, such as, e.g., nitrous oxide, can be supplied by gas conduit system 40 to bathe cornea 26 in a cool environment and thereby lower the metabolic state of the cornea. Lowering the metabolic state of cornea 26 enhances the ability of the cornea to withstand traumatic insults from the beam.

To monitor the length and intensity of the beams directed onto the external surface of cornea 26 or onto the intrastromal areas of cornea 26 by apparatus 10, a plurality of linear detector arrays 58 can be installed. As seen in FIG. 3, apparatus 32 includes frustoconical surface 60 adapted to partially reflect a small portion (about 5%) of the beams directed towards cornea 26 by peripheral reflectors. Surface 60 further reflects these small portions of the beams against linear detectors 58 which are coupled to a detector means 59 for determining the beam intensity distribution and length. Preferably, three detectors 58 are used, which are rigidly coupled to ring 21.

As seen in FIG. 3, the peripheral reflectors 14a'-h' are modified from those shown in FIGS. 1 and 2 by having a curved reflective surface 15' curved about an axis B which is perpendicular to axis A. This curvature about axis B approximates the curvature of the external surface of the cornea being ablated and provides a more even ablation and beam intensity incident on the cornea. The radius of curvature of the reflective surface 15' about axis B reduces in the radially inward direction so the reflected line focus is substantially coincident or parallel to with the outer surface of the cornea. Reflective surface 15' is also curved and preferably semi-cylindrical about axis A.

Beam delivering apparatus 10 of FIG. 3 therefore permits more precision in the radial keratotomy procedure than existing systems which interpose a mask between the beam source and the cornea. Unlike the beams produced by the existing systems, each portion of the beam reaching cornea 26 is substantially uniformly focused on or in the cornea in a curved line focus. Thus, the distribution of energy along the incision is substantially uniform and can therefore be more precisely controlled.

Figure 4:
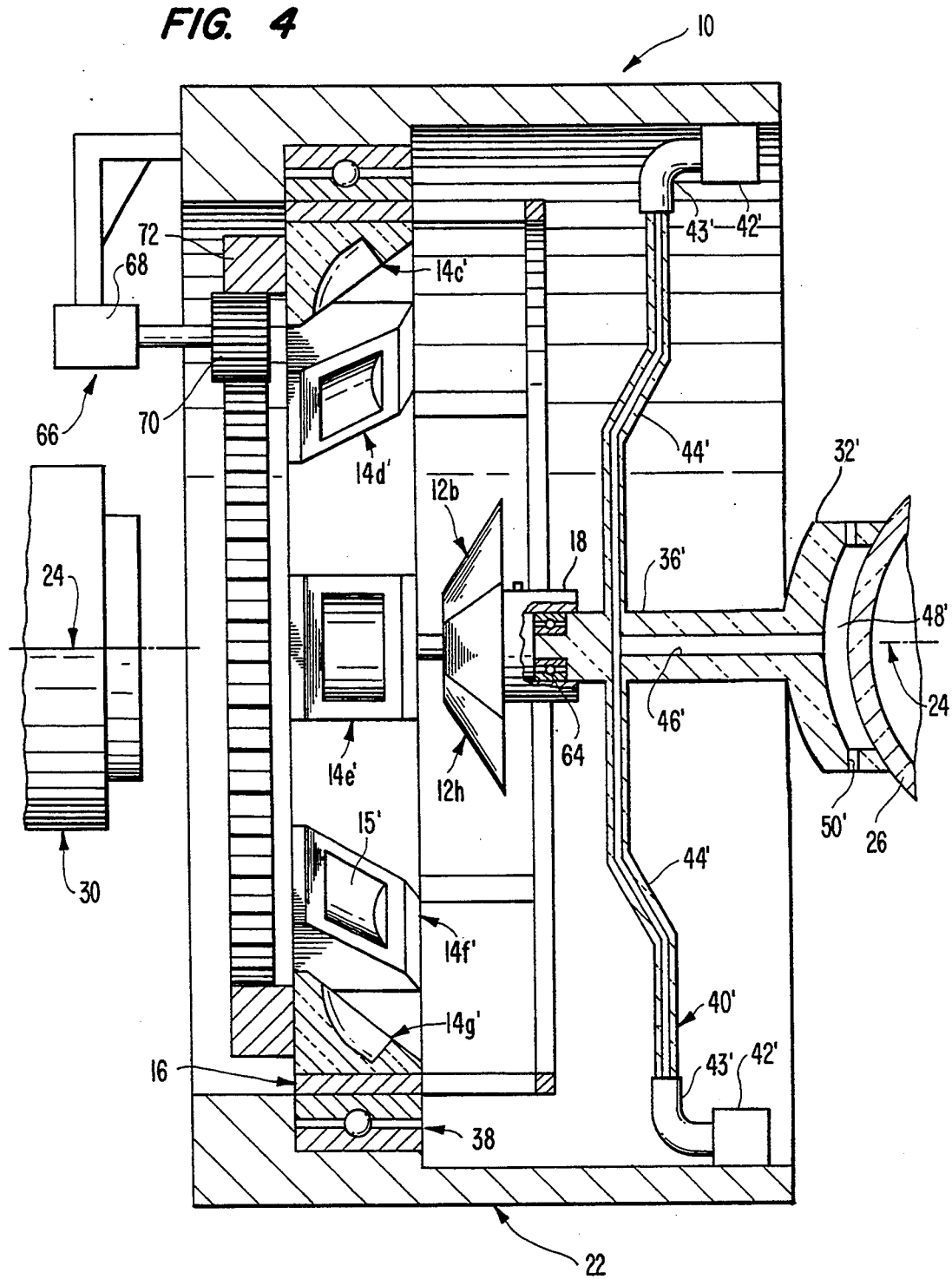
FIG. 4 is a cross-sectional side view of another modification of the apparatus of FIG. 1, showing a second gas conduit delivery system for delivering gas to the cornea of the eye during rotation of the reflectors.

Embodiment of FIG. 4

With reference now to the use of beam delivering apparatus 10 in an eye lathing, or scanning, operation as shown in FIG. 4, apparatus 10 can be especially adapted for scanning an eye. In the embodiment shown in FIG. 4, gas conduit system 40' is constructed with its conduits 44' remote from spokes 20, in contrast to the embodiment shown in FIG. 3 in which conduit 44 is formed within one of the spokes 19. Ball bearing assembly 64 is provided at the connection of connecting stem 36' and hub 18 so that the central and peripheral reflectors can rotate relative to eye positioning device 32'.

Figure 12:
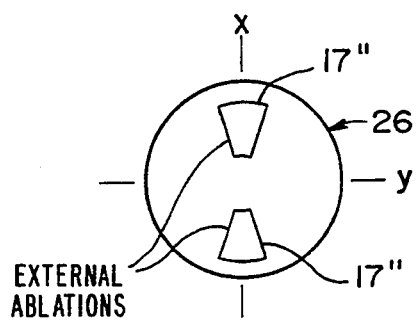
FIG. 12 is a schematic view of a cornea having wedge-shaped ablations on the external surface of the cornea formed by focusing and pivoting radial lines of radiant energy onto external areas of the cornea.

Additionally, a drive assembly 66 having a drive motor 68 for rotating a gear 70 is provided. Gear 70 meshes with a ring gear 72 which is rigidly connected to the sides of the peripheral reflectors. Drive motor 68 is preferably a reversible, stepping motor which allows for incremental rotation of central reflectors 12a–h together with peripheral reflectors 14a–h. Accordingly, the radial lines focused on either the external or internal areas of the cornea can be rotated 360° or pivoted a few degrees in either direction for removing selected portions of the cornea. For example, a pair of radial lines can be focused onto the cornea and pivoted approximately eight degrees from both sides of the X axis to ablate a pair of wedge-shaped incisions 17" as seen in FIG. 12. Of course, cornea 26 can be ablated to remove areas of the cornea having a variety of configurations depending upon various factors such as the number and position of lines, and the amount of rotation.

Figure 7:
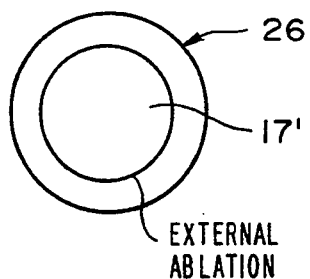
FIG. 7 is a schematic representation of a cornea having a lenticular ablation after scanning the radiant energy bees directed onto the cornea by the apparatus of FIG. 4.

To obtain the scanning pattern schematically shown in FIG. 7 as a full lenticular ablation, drive motor 68 is operated to rotate gear 70 which, in turn, rotates ring 72 to rotate reflectors 12a–h and 14a–h about axis 24. Preferably, the reflectors are rotated at a rate of approximately 200 revolutions per minute. However, rotation speed is preferably selected for the given beam focusing width on the cornea to remove material continuously over the cornea. Conduits 44' can be formed from plates or tubes which are transparent to the radiant energy beam so they do not interfere with the beach. The scanning incision 17' is shown in FIG. 7 and is in the form of a lenticular ablation in the shape of a positive, negative or toxic lens. This ablation includes the full surface of the cornea, although a central part can be omitted, thereby providing an annular ablation. As used herein, "lenticular ablation" means removing corneal material via laser photoablation in the shape of an optical lens.

Figure 5:
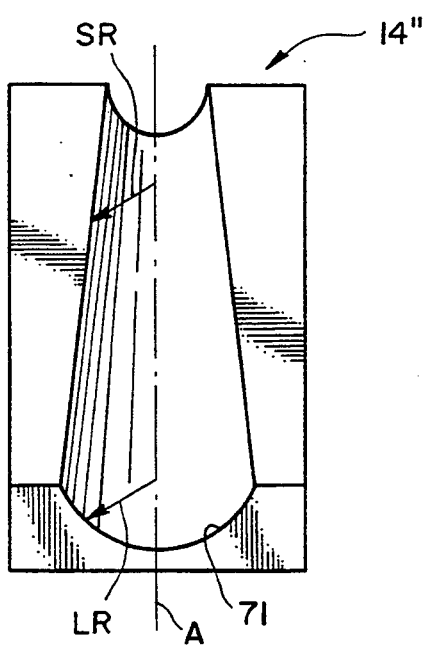
FIG. 5 is a perspective view of a modified peripheral reflector for use in the apparatus of FIG. 1, showing the change in the radius of curvature of the reflector along its central axis A.

Embodiment of FIG. 5

To more precisely tailor the curved line focus of the beams reflected from the peripheral reflectors so that corneas of differing radii of curvature can be accommodated, each peripheral reflector can be designed with a curved reflective surface whose curvature varies along the length of the reflector along central axis A. As shown in FIG. 5, peripheral reflector 14" has a concave surface 71 varying from a smaller radius SR to a larger radius LR. Accordingly, the beams reflected onto the external surface or onto the intrastromal areas of the cornea 26 from reflectors 14" produce radial incisions of desired curved line focus and thus intensity therealong. Reflectors 14" accomplish similar result as reflectors 14a'–h' as seen in FIG. 3 but via a different reflector configuration.

As shown in FIG. 1, the central reflectors can also be provided with four inner and four outer alignment detectors 73 and 74 which monitor the alignment of the reflectors with respect to the beam incident thereon to allow adjustment of the laser beam to the optical center thereof.

The beam delivering apparatus 10 of the present invention controls and focuses the beam on the corneal surface or on intrastromal areas. This is beneficial since the greater the amount of energy radiated onto the cornea, the greater the risk that the cornea will be damaged by overheating or, in the case of ultraviolet radiation, by overshock.

The overall delivery system is quite compact and can be enclosed between the laser 30 and gas conduit system 40' shown in FIG. 4. This allows filling of the whole beam delivering system with a neutral gas to minimize ozone build-up by ultraviolet radiation.

As seen by comparing FIGS. 2 and 4, the arrangement of the central and peripheral reflectors is the same for radial keratotomy and lathing via scanning. The only difference in these procedures is the rotation of the central and peripheral reflectors during scanning.

Embodiment of FIG. 9

Referring now to the beam delivering apparatus 110 as shown in FIG. 9, apparatus 110 is substantially identical to the beach delivering apparatus 10 of FIG. 3, except that peripheral reflectors 14a'–h' have been replaced with peripheral reflectors 114a and 114b to simultaneously forth two circumferentially curved incisions on areas of a cornea. The circumferentially curved incisions can be formed either on the external surface of a cornea or on intrastromal areas of a cornea.

Specifically, beam delivering apparatus 110 as seen in FIG. 9 includes a pair of central reflectors 112a and 112b and an annular assembly of peripheral reflectors 114a and 114b. Peripheral reflectors 114a and 114b are rigidly coupled to a rim 116. Rim 116 is rigidly coupled to a hub 118 by radial spokes 119, axial rods 120 and a ring 121. Central reflectors 112a and 112b are coupled to hub 118.

Beam delivering apparatus 110 is rotatably supported within a support or frame 122 about a main optical axis 124 which passes through the center of a cornea 126 of an eye. A laser beam source 130, such as a frequency modified YAG laser for ablating external surface areas of the cornea or a frequency-doubled YAG laser for ablating intrastromal areas of the cornea, is positioned to emit a beam along axis 124 and against central reflectors 112a and 112b. These reflectors split and reflect the beam onto peripheral reflectors 114a and 114b which then focus and reflect the split beams onto an area of cornea 126 in a curvilinear configuration.

Referring now more specifically to the construction and orientation of central reflectors 112a and 112b and peripheral reflectors 114a and 114b for performing an operation to correct an astigmatism. A pair of equal sized central reflectors 112a and 112b are provided. While only two central reflectors are illustrated, the number of central reflectors can be any even number more than two and less than 16.

As shown in FIG. 9, two equally sized central reflectors 112a and 112b are rigidly coupled to one another along a pair of opposite sides by a pair of connecting members 113 (only one shown) to form a wedge-shaped mirror centered on axis 124. Each central reflector 112a and 112b is oriented to present a slanted, outwardly facing flat surface to the beam emanating from beam source 130. The angle of each surface is about 50°–60° to axis 124.

Each peripheral reflector 114a and 114b is associated with one of the central reflectors 112a and 112b and is oriented so that its reflective surface 115 intercepts the beam reflected radially, outwardly by its associated central reflector. Additionally, each peripheral reflector is oriented and constructed so as to reflect the intercept beam axially and radially inward and to focus the beam into line focus either onto the external surface of cornea 126 or onto an intrastromal area of the cornea. The line focus of each beam onto cornea 126 is a curvilinear line which is preferably circumferentially curved about the optical axis 124. Preferably, the centers of the circumferentially curved lines focused on cornea 126 are located on optical axis 124.

The reflective surfaces of the central and peripheral reflectors can be curved mirrors or other reflective material which focuses the beam in a curvilinear configuration onto either an external or internal areas of the cornea. For example, the peripheral reflectors 114a and 114b as shown in FIG. 9 are holographic elements or mirrors, which focus circumferential curved lines onto areas of the cornea. Holographic elements or mirrors 114a and 114b can be constructed with a flat reflective surface 115 having different reflective indexes along reflective surface 115 so that a variety of shapes and orientations of lines can be focused onto either external or internal areas of the cornea, including curvilinear lines and rectilinear lines.

Figure 10:
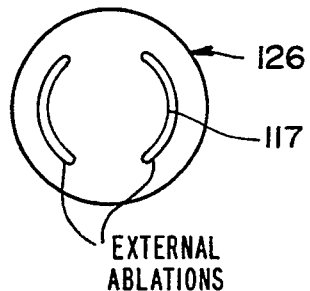
FIG. 10 is a schematic view of a cornea having circumferentially curved incisions on the external surface of the cornea.
Figure 11:
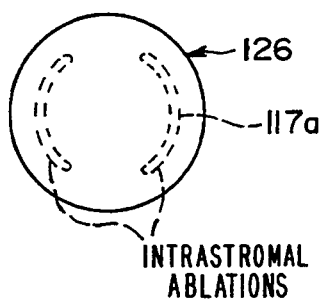
FIG. 11 is a schematic view of a cornea having circumferentially curved incisions on intrastromal areas of the cornea.

As schematically shown in FIG. 10, a two circumferentially curved incisions 117 are cut via photoablation in the external surface of cornea 126 during an operation to correct an astigmatism. Alternatively, two circumferentially curved, intrastromal incisions 117a can be cut via photoablation in intrastromal areas of cornea 126 during an operation to correct an astigmatism, as schematically illustrated in FIG. 11.

Beam delivering apparatus 110 can be used to produce the external or intrastromal incisions simultaneously. As seen in FIG. 9, each central reflector 112a and 112b intercepts the beam and reflects the beam towards its associated peripheral reflector 114a and 114b. Central reflectors 112a and 112b are preferably rotatably coupled to hub 118 via an axle 153 fitting into the hub 118 and a screw adjustment assembly including three set screws 156 to lock the reflectors relative to hub 118. Central reflectors 112a and 112b can be moved as a single unit relative to hub 118 and the adjustment screws 156 can then be operated to adjust and fix the relative position of the central reflectors relative to the peripheral reflectors.

The combination of central and peripheral reflectors including the rim 116, hub 118, spokes 119, rods 120 and ring 121 are supported for rotation relative to frame 122 via ball bearing assembly 138, which is coupled to the frame and to rim 116. Thus, the angular position of the reflectors relative to cornea 126 and axis 124 can be varied. This allows angular placement as desired of either external incisions 117 on the cornea or intrastromal incisions 117a in the cornea.

The operation of beam delivering apparatus 110 during a simple operation to correct an astigmatism is as follows. Cornea 126 is immobilized by appropriate means and laser beam source 130 is positioned to emit a beam along main optical axis 124, which passes through the center of cornea 126. Beam directing apparatus 110 is positioned between beam source 130 and cornea 126 and is appropriately spaced from cornea 126 so that the beams reflected by the central and peripheral reflectors ablate cornea 126 in a pattern comprising separate and discrete areas of ablation shown in FIG. 10 or FIG. 11. Once beam directing apparatus 110 is positioned, a test beam can be emitted to test the alignment of the beams on cornea 126. Beam source 130 is then operated to emit a radiant energy beam, such as a laser beam, which travels along axis 124, encounters the central reflectors 112a and 112b, is split and radially reflected against peripheral reflectors 114a and 114b and is then again radially reflected and focused either onto the external surface of cornea 126 to simultaneously make external incisions 117 or onto intrastromal areas of cornea 126 to simultaneously make intrastromal incisions 117a.

A drive assembly 166 having a drive motor 168 for rotating a gear 170 is provided. Gear 170 meshes with a ring gear 172 which is rigidly connected to the sides of the peripheral reflectors. Drive motor 168 is preferably a reversible, stepping motor which allows for incremental rotation of central reflectors 112a and 112b together with peripheral reflectors 114a and 114b. Accordingly, the circumferentially curved lines, which are focused on either external or internal areas of the cornea, can be rotated 360° or pivoted a few degrees to remove selected portions of the cornea.

It should be apparent to those skilled in the art that a plurality of curvilinear lines can be focused onto the cornea at various positions to ablate the cornea as required to correct the patient's vision.

Beam delivering apparatus 110 and eye positioning apparatus 132 can be provided with a gas or fluid conduit system 140 for delivering selected gases to the cornea 126 during ablation. Gas conduit system 140 includes a gas supply means 142 to supply gas along a tube 143 and a conduit 144 mounted within one of the spokes 119. Conduit 144 communicates with an axial conduit 146 within eye positioning apparatus 132 and axial conduit 146 communicates with a substantially semihemispheric recess 148 defined by concave surface 134. Recess 148 communicates with conduit 146 and cornea 126 and has outlets 150 for exhausting gases which have contacted cornea 126.

An inert gas such as argon can be supplied by gas conduit system 140 to contact cornea 126 and remove debris and other by-products of the surgical operation. Additionally, a gas or liquid having a cold temperature, such as, e.g., nitrous oxide, can be supplied by gas conduit system 140 to bathe cornea 126 in a cool environment and thereby lower the metabolic state of the cornea. Lowering the metabolic state of cornea 126 enhances the ability of the cornea to withstand traumatic insults from the beam.

While various advantageous embodiments have been chosen to illustrate the invention, it will be understood by those skilled in the art that various changes and modifications can be made therein without departing from the scope of the invention as defined in the appended claims.

What is claimed is:

1. An apparatus for delivering radiant energy beams onto an area of a cornea of an eye centered on a main optical axis, the combination comprising:

a source of radiant energy beam aimed along the main optical axis;

a support;

an array of discrete central reflector means, arranged about the main optical axis, for intercepting the radiant energy beam incident thereon, splitting the beam into a plurality of beam portions, and reflecting each beam portion outwardly of the main optical axis;

first means, coupled to said support and said array of central reflector means, for coupling said central reflector means to said support;

an assembly of discrete peripheral reflector means, outwardly spaced from said central reflector means, each peripheral reflector means for intercepting one of said reflected beam portions from an associated central reflector means and for directing said intercepted beam portion generally along the main optical axis and for incidence onto an area of the cornea; and second means, coupled to said support and said peripheral reflector means, for coupling said peripheral reflector means to said support, each of said peripheral reflector means including means for focusing said intercepted beam portion onto an area of the cornea separate and discrete from the incidence of remaining said intercepted beam portions reflected onto areas of the cornea and in a linear configuration.

2. An apparatus according to claim 1, wherein said second means comprises means for supporting said array of central reflector means for angular movement relative to said assembly of peripheral reflector means.

3. An apparatus according to claim 1, wherein said first and second means comprises means, coupled to said array of central reflector means and said assembly of peripheral reflector means, for fixedly interconnecting said array and said assembly, and means for rotatably supporting said interconnected array and assembly on said support for rotation about the main optical axis, and means for rotating said interconnected array and assembly.

4. An apparatus according to claim 1, wherein said central reflector means are mirrors.

5. An apparatus according to claim 1, wherein said peripheral reflector means are mirrors.

6. An apparatus according to claim 1, wherein said central reflector means have flat reflective surfaces.

7. An apparatus according to claim 1, wherein each of said means for focusing comprises a curved reflective surface.

8. An apparatus according to claim 1, wherein each of said means for focusing comprises a substantially semi-cylindrical reflective surface.

9. An apparatus according to claim 1, wherein each of said means for focusing comprises a reflective surface that is curved about an axis A and is curved about an axis B which is perpendicular to axis A.

10. An apparatus according to claim 1, wherein each of said means for focusing comprises a reflective surface that is curved about an axis A, and having a radius of curvature varying therealong.

11. An apparatus according to claim 1, and further comprising
said peripheral reflector means are holographic elements.

12. An apparatus according to claim 1, wherein said array of central reflector means includes from two to eight central reflector means, and
said assembly of peripheral reflector means includes from two to eight peripheral reflector means.

13. An apparatus according to claim 1, wherein said array of central reflector means is an octagonal array.

14. An apparatus according to claim 1, and further comprising
means, coupled to said support, for reflecting a part of the beams reflected by said peripheral reflector means and determining the length of the beams from the source and the energy distribution of the beams.

15. An apparatus according to claim 1, and further comprising
an eye positioning device coupled to said support for positioning the cornea relative to said central reflector means.

16. An apparatus according to claim 15, and further comprising
conduit means coupled to said eye positioning device for delivering fluid to the cornea.

17. An apparatus according to claim 1, wherein each of said means for focusing is configured to focus said intercepted beam portion onto an external area of the cornea for ablating an external surface of the cornea.

18. An apparatus according to claim 17, wherein said first and second means comprises means, coupled to said array of central reflector means and said assembly of peripheral reflector means, for fixedly interconnecting said array and said assembly, and means for rotatably supporting said interconnected array and assembly on said support for rotation about the main optical axis, and means for rotating said interconnected array and assembly.

19. An apparatus according to claim 17, wherein each of said means for focusing is further configured to focus said intercepted beam portion in a rectilinear configuration on the cornea.

20. An apparatus according to claim 19, wherein each of said means for focusing is further configured to focus said intercepted beam portion along a line extending radially, outwardly from the main optical axis of the cornea.

21. An apparatus according to claim 17, wherein each of said means for focusing is further configured to focus said intercepted beam portion in a curvilinear configuration on the cornea.

22. An apparatus according to claim 21, wherein each of said means for focusing is further configured to focus said intercepted beam portion along a line extending radially, outwardly from the main optical axis of the cornea.

23. An apparatus according to claim 22, wherein said first and second means comprises means, coupled to said array of central reflector means and said assembly of peripheral reflector means, for fixedly interconnecting said array and said assembly, and means for rotatably supporting said interconnected array and assembly on said support for rotation about the main optical axis, and means for rotating said interconnected array and assembly.

24. An apparatus according to claim 21, wherein each of said means for focusing is further configured to focus said intercepted beam portion along a circumferentially curved line on the cornea.

25. An apparatus according to claim 24, wherein said first and second means comprises means, coupled to said array of central reflector means and said assembly of peripheral reflector means, for fixedly interconnecting said array and said assembly, and means for rotatably supporting said interconnected array and assembly on said support for rotation about the main optical axis, and means for rotating said interconnected array and assembly.

26. An apparatus according to claim 1, wherein
each of said means for focusing is configured to focus said intercepted beam portion onto an intrastromal area of the cornea without ablating an external surface of the cornea.

27. An apparatus according to claim 26, wherein
each of said means for focusing is further configured to focus said intercepted beam portion in a rectilinear configuration onto the intrastromal area of the cornea.

28. An apparatus according to claim 27, wherein
each of said means for focusing is further configured to focus said intercepted beam portion along a line extending radially, outwardly from the main optical axis of the cornea.

29. An apparatus according to claim 28, wherein
said first and second means comprises means, coupled to said array of central reflector means and said assembly of peripheral reflector means, for fixedly interconnecting said array and said assembly, and means for rotatably supporting said interconnected array and assembly on said support for rotation about the main optical axis, and
means for rotating said interconnected array and assembly.

30. An apparatus according to claim 26, wherein
each of said means for focusing is further configured to focus said intercepted bee portion in a curvilinear configuration onto the intrastromal area of the cornea.

31. An apparatus according to claim 30, wherein
each of said means for focusing is further configured to focus said intercepted beam portion along a line extending radially, outwardly from the main optical axis of the cornea.

32. An apparatus according to claim 31, wherein
said first and second means comprises means, coupled to said array of central reflector means and said assembly of peripheral reflector means, for fixedly interconnecting said array and said assembly, and means for rotatably supporting said interconnected array and assembly on said support for rotation about the main optical axis, and
means for rotating said interconnected array and assembly.

33. An apparatus according to claim 30, wherein
each of said means for focusing is further configured to focus said intercepted beam portion along a circumferentially curved line onto the intrastromal area of the cornea.

34. An apparatus according to claim 33, wherein
said first and second means comprises means, coupled to said array of central reflector means and assembly of peripheral reflector means, for fixedly interconnecting said array and said assembly, and means for rotatably supporting said interconnected array and assembly on said support for rotation about the main optical axis, and
means for rotating said interconnected array and assembly.

35. A method of ablating an area of a cornea via a radiant energy beam, comprising the steps of
aligning a source of radiant energy beam and the cornea along a main axis,
emitting the radiant energy beam from the source,
splitting the beam into a plurality of beam portions and reflecting those beam portions outwardly of the main axis,
reflecting the outwardly directed beam portions generally along the main axis to produce a plurality of output beam portions, and
directing and focusing each of the output beam portions for incidence onto the cornea in an area separate and discrete from the incidence of remaining output beam portions reflected onto areas of the cornea and in a linear configuration.

36. A method according to claim 35, wherein
the directing and focusing step includes focusing the output beam portions onto intrastromal areas of the cornea for ablating the intrastromal areas without ablating an external surface of the cornea.

37. A method according to claim 36, wherein
the directing and focusing step includes focusing the output beam portions in a rectilinear configuration onto the intrastromal areas of the cornea.

38. A method according to claim 37, wherein
the directing and focusing step includes focusing the output beam portions along a line extending radially, outwardly from the main optical axis of the cornea.

39. A method according to claim 38, wherein
the splitting, the two reflecting, and the directing and focusing steps include the step of revolving the output beam portions about the main optical axis of the cornea.

40. A method according to claim 36, wherein
the directing and focusing step includes focusing the output beam portions in a curvilinear configuration onto the intrastromal areas of the cornea.

41. A method according to claim 40, wherein
the directing and focusing step includes focusing the output beam portions along a line extending radially, outwardly from the main optical axis of the cornea.

42. A method according to claim 41, wherein
the splitting, the two reflecting, and the directing and focusing steps include the step of revolving the output beam portions about the main optical axis of the cornea.

43. A method according to claim 40, wherein
the directing and focusing step includes focusing the output beam portions along a circumferential curved line onto the intrastromal areas of the cornea.

44. A method according to claim 43, wherein
the splitting, the two reflecting, and the directing and focusing steps include the step of revolving the output beam portions about the main optical axis of the cornea.

45. A method according to claim 35, wherein
the directing and focusing step includes focusing the output beam portions onto external areas of the cornea for ablating the external areas of the cornea.

46. A method according to claim 45, wherein
the directing and focusing step includes focusing the output beam portions in a rectilinear configuration on the cornea.

47. A method according to claim 46, wherein
the directing and focusing step includes focusing the output beam portions along a line extending radially, outwardly from the main optical axis of the cornea.

48. A method according to claim 47, wherein
the splitting, the two reflecting, and the directing and focusing steps include the step of revolving the output beam portions about the main optical axis of the cornea.

49. A method according to claim 45, wherein the directing and focusing step includes focusing the output beam portions in a curvilinear configuration on the cornea.

50. A method according to claim 49, wherein the directing and focusing step includes focusing the output beam portions along a line extending radially, outwardly from the main optical axis of the cornea.

51. A method according to claim 50, wherein the splitting, the two reflecting, and the directing and focusing steps include the step of revolving the output beam portions about the main optical axis of the cornea.

52. A method according to claim 49, wherein the directing and focusing step includes focusing the output beam portions along a circumferential curved line on the cornea.

53. A method according to claim 52, wherein the splitting, the two reflecting, and the directing and focusing steps include the step of revolving the output beam portions about the main optical axis of the cornea.

* * * * *